United States Patent
Ingimundarson et al.

(10) Patent No.: US 9,554,933 B2
(45) Date of Patent: Jan. 31, 2017

(54) STRAP TIGHTENER ASSEMBLY FOR AN ORTHOPEDIC DEVICE

(71) Applicant: Össur hf, Reykjavik (IS)

(72) Inventors: Arni Thor Ingimundarson, Gardabaer (IS); Sindri Pall Sigurdsson, Reykjavik (IS); Janaki Ram-srinivasaRao Chetlapalli, Irving, CA (US); Jason Robert Taylor, Aliso Viejo, CA (US); Shireen Maria Palsson, Irvine, CA (US)

(73) Assignee: Össur hf, Reykjavik (IS)

( * ) Notice: Subject to any disclaimer, the term of this patent is extended or adjusted under 35 U.S.C. 154(b) by 485 days.

(21) Appl. No.: 13/739,491

(22) Filed: Jan. 11, 2013

(65) Prior Publication Data

US 2013/0184628 A1    Jul. 18, 2013

Related U.S. Application Data

(60) Provisional application No. 61/586,662, filed on Jan. 13, 2012, provisional application No. 61/667,522, filed on Jul. 3, 2012.

(51) Int. Cl.
*A61F 5/01* (2006.01)

(52) U.S. Cl.
CPC ........... *A61F 5/0123* (2013.01); *A61F 5/0102* (2013.01)

(58) Field of Classification Search
CPC ...... A44B 11/065; A44B 11/10; A43C 11/165
USPC  24/68 SK, 71.1, 909, 714.6–714.9; 36/50.1, 50.5
See application file for complete search history.

(56) References Cited

U.S. PATENT DOCUMENTS

| 4,884,731 | A | * | 12/1989 | Sibley ........................... 224/651 |
| 5,277,698 | A |   | 1/1994  | Taylor |
| 7,198,610 | B2 |  | 4/2007  | Ingimundarson et al. |
| 7,992,261 | B2 |  | 8/2011  | Hammerslag et al. |
| D712,048  | S | * | 8/2014  | Sigurdsson et al. ......... D24/190 |
| 2005/0279797 | A1 | * | 12/2005 | Martin et al. ................. 224/637 |
| 2009/0256892 | A1 | * | 10/2009 | Takeuchi ........................ 347/86 |
| 2009/0287128 | A1 |   | 11/2009 | Ingimundarson et al. |

FOREIGN PATENT DOCUMENTS

WO      2009139895 A1    11/2009

OTHER PUBLICATIONS

International Search Report from corresponding PCT Application No. PCT/US2013/021103 dated Apr. 12, 2013.

* cited by examiner

*Primary Examiner* — Alireza Nia
*Assistant Examiner* — Camtu Nguyen
(74) *Attorney, Agent, or Firm* — Workman Nydegger

(57) ABSTRACT

A strap tightener assembly has a base, a tightening device mounted on the base and movable relative thereto, and a strap assembly coupled to the tightening device. The tightening device provides incremental movement of the strap assembly relative to the base at a plurality of predefined settings. A cover extends over the strap assembly and connects to the base so that the base and the cover form a channel permitting movement of the strap assembly therethrough. The cover defines an elongate slot extending along a portion of a length of the cover, and the strap assembly has an indicator identifying the relative location of the strap assembly to the cover. A strap is securable to the strap assembly.

6 Claims, 8 Drawing Sheets

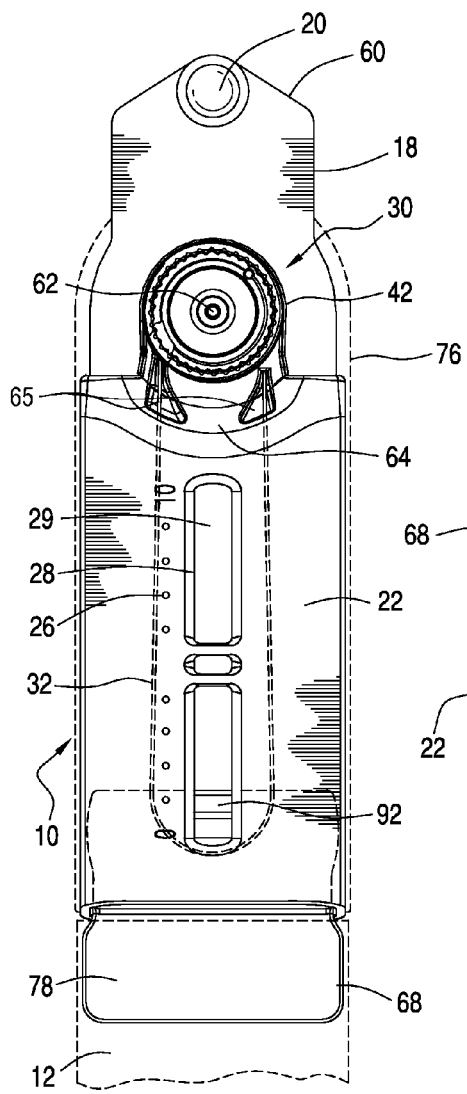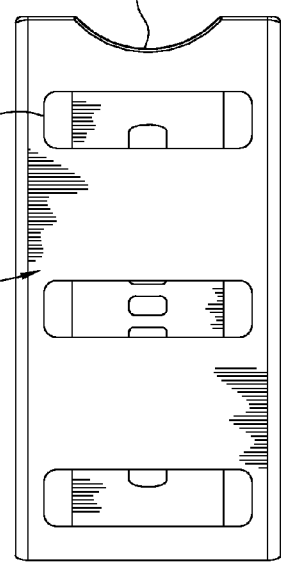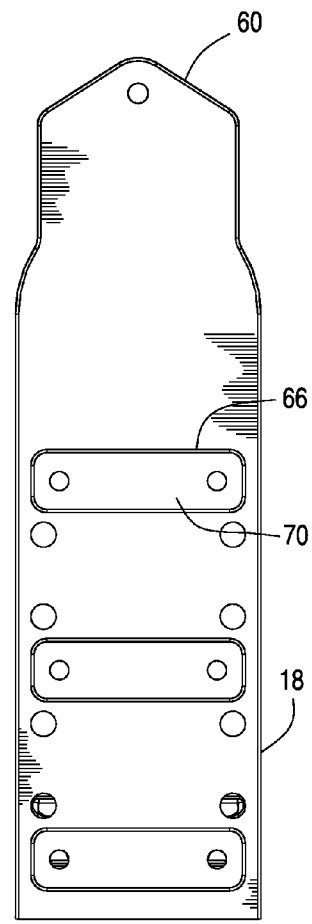
FIG. 8A
FIG. 8B
FIG. 8C
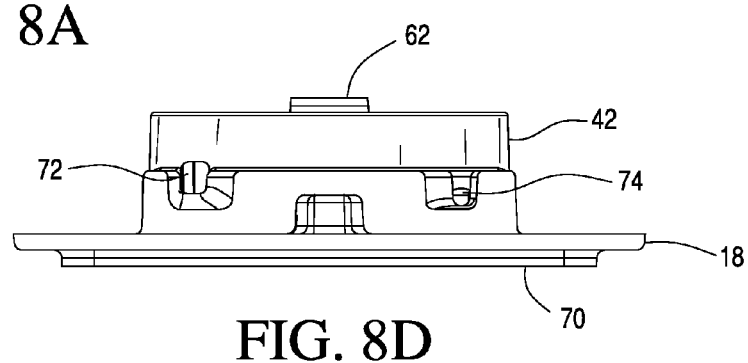
FIG. 8D

STRAP TIGHTENER ASSEMBLY FOR AN ORTHOPEDIC DEVICE

FIELD OF ART

This disclosure relates to a strap tightener assembly for an orthopedic device for tightening a strap used to secure the orthopedic device on a wearer.

BACKGROUND

Knee braces are widely used to treat a variety of knee infirmities. Such braces may be configured to impart forces or leverage on the limbs surrounding the knee joint to relieve compressive forces within a portion of the knee joint, or to reduce the load on that portion of the knee. In the event that knee ligaments are weak and infirm, a knee brace may stabilize, protect, support, unload, and/or rehabilitate the knee.

The knee is acknowledged as one of the weakest joints in the body, and serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any kind of physical activity requiring using the legs.

A healthy knee has an even distribution of pressure in both the medial and lateral compartments of the knee. It is normal for a person with a healthy knee to place a varus moment on the knee when standing so the pressure between the medial and lateral compartments is uneven but still natural.

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or due to aging of the knee.

A major problem resulting from osteoarthritis of the knee is that the smooth cartilage lining the inside of the knee wears away. This leads to a narrowing of the joint space with developing cysts and erosions in the bone ends. Because of the narrowing of the joint, bone comes directly in contact with bone, and an uneven distribution of pressure develops across the knee which may cause the formation of bone spurs around the joint. All of these changes ultimately lead to increasing pain and stiffness of the joint.

While there are no cures to osteoarthritis, there are many treatments. Individuals who have diagnosis of isolated medial or lateral compartmental osteoarthritis of the knee are confronted with a variety of treatment options such as medications, surgery, and nonsurgical interventions. Nonsurgical interventions include using canes, lateral shoe wedges, and knee bracing.

Knee bracing is useful to provide compartmental pain relief by reducing the load on the affected compartment through applying an opposing external valgus or varus moment about the knee joint. Unloading knee braces have been shown to significantly reduce osteoarthritis knee pain while improving knee function.

In these unloading braces, straps fasten the brace to the limb and enable the strap to exert forces on the knee to unload the affected compartment of the knee. The tension in a strap affects the function, fit and comfort of the brace, especially when the strap is used to unload the knee. Inadequate tension may diminish the effectiveness of the brace to not only unload the knee but to stabilize the brace as well, whereas excessive tension may cause discomfort to the wearer. It would be beneficial to provide a device that indicates how much tension is in a strap and provide means by which the tension of the strap can be easily controlled.

The prior art suffers from disadvantages of providing adequate means for identifying the tension level or tightening in a strap, and rarely allows for incremental tensioning control of the strap at a plurality of predefined settings.

SUMMARY

In an embodiment of the strap tightener assembly, the assembly includes an elongate base having first and second ends, a tightening device having incremental control at a plurality of predefined settings and mounted on the base near the first end and movable relative thereto, and a strap assembly having a first end coupled to the tightening device and moved linearly relative to the base. The strap assembly carries a strap. An indicator may be provided which allows for a measure of displacement of the strap assembly relative to the base.

The strap tightener assembly may include a cover extending over the strap assembly and interlockingly connected to the base. The base and the cover form a channel permitting movement of the strap assembly therethrough so that the strap assembly carrying the strap may be contained or confined within the channel over its course of movement.

The base may include a housing for receiving the tightening device. A cable may be rotatably secured and windable about the tightening device. The cable secures at one end to the strap assembly and the housing defines at least one opening along a side for permitting passage of the cable therethrough.

The strap tightener assembly may be considered substantially flexible having at least a majority of its length which can yield to the shape of a wearer's anatomy as the strap is tightened thereagainst. While some components, such as the tightening device may not be or have less flexibility than the base and the cover, the strap tightener assembly when considered as a whole can flex.

The strap may be formed from a textile and have a width substantially greater than a width of the cable. The textile-based strap may have at least one surface formed from hook receivable material. The strap assembly may include an indicator slidably fitting within an elongate slot of the cover. A plurality of indicia may be located along the elongate slot and the indicator slides relative to the indicia to indicate tension levels of the strap assembly.

The strap assembly and the base may be formed from a flexible polymeric material, and the cover may be formed from a flexible polymeric material or a textile. In a variation, the base is formed from a material harder than the cover.

The strap tightener assembly may be considered substantially flexible having at least a majority of its length which can yield to the shape of a wearer's anatomy as the strap is tightened thereagainst. While some components, such as the tightening device may not be or have less flexibility than the base and the cover, the strap tightener assembly when considered as a whole can flex and resiliently return to shape.

According to an embodiment, the cover defines a plurality of openings along a back surface, and the base has a plurality of protrusions interlockingly engaging the cover at the plurality of openings. Fastener elements may be on the plurality of protrusions such that the fastener elements extend outwardly from the strap tightener assembly.

The orthopedic device disclosed may be of an unloading type knee brace, under the principles described in U.S. Pat. No. 7,198,610, granted Apr. 3, 2007, and U.S. Pat. No. 5,277,698, granted Jan. 11, 1994, both incorporated herein in their entirety by reference. The disclosure and the strap tightener assembly described herein can be employed in a variety of orthopedic devices outside of unloading type knee braces, and the principles can be yet further extended to any application including incremental control of a strap.

An additional strap tightener assembly may be used in any part of the orthopedic device, and particular for circumferentially adjusting a strap. A tightening device may be secured on a frame member and adjustably secured to a strap assembly or strap which is connected to the same frame member or another frame member. By adjusting the tightening device, the strap or strap assembly can be tightened or loosened accordingly. In a variation, the strap assembly includes a first strap segment secured to a cable retainer and a second strap segment is adjustably secured to the first strap segment. Substantial adjustments can be made by securing the second strap segment to various locations on the first strap segment, or vice versa, and then small adjustments may be made by the tightening device.

A cable connecting the tightening device to the strap or strap assembly may be concealed by a sleeve covering at least a portion of the frame member or the cable may extend through portions of the frame member.

BRIEF DESCRIPTION OF THE DRAWINGS

The strap tightener assembly for an orthopedic device is described referring to the accompanying drawings which show preferred embodiments according to the device described. The device as disclosed in the accompanying drawings is illustrated for example only. The elements and combinations of elements described below and illustrated in the drawings can be arranged and organized differently to result in embodiments still within the spirit and scope of the device described.

FIG. 8A is a plan frontal view of an embodiment of a casing and base for a strap tightener assembly.

FIG. 8B is a rear plan view of the cover in FIG. 8A.

FIG. 8C is a rear plan view of the base in FIG. 8A.

FIG. 8D is a frontal elevational view of the base in FIG. 8A.

DETAILED DESCRIPTION OF VARIOUS EMBODIMENTS

A. Overview

Figure 1:
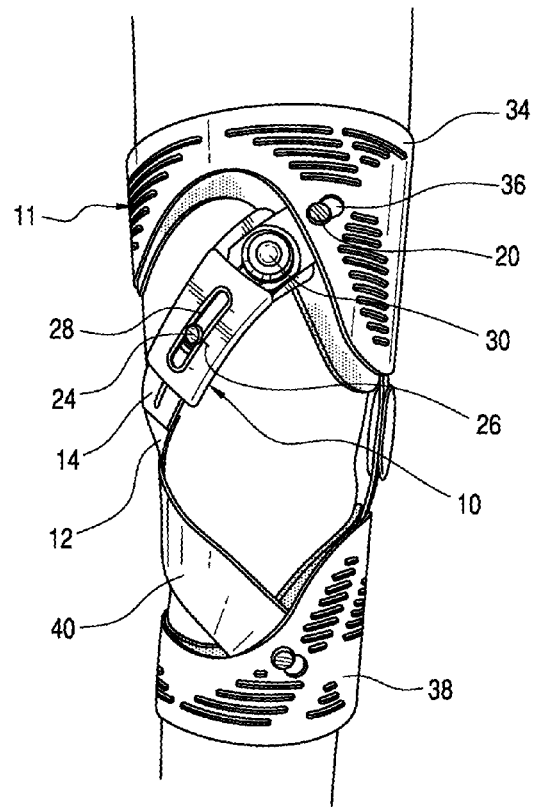
FIG. 1 is a perspective view showing a strap tightener assembly on an orthopedic device.

A better understanding of different embodiments of the strap tightener assembly may be had from the following description read in conjunction with the accompanying drawings in which like reference characters refer to like elements.

While the disclosure is susceptible to various modifications and alternative constructions, certain illustrative embodiments are shown in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Definitions

For ease of understanding the disclosed embodiments of an orthopedic device used as the exemplary application for the strap tightener assembly, the anterior and posterior portions of the orthopedic device are described independently. The anterior and posterior portions of the orthopedic device function together to support and stabilize anatomical portions of the wearer of the device.

For further ease of understanding the embodiments of an orthopedic device as disclosed, a description of a few terms may be necessary. The term "proximal" has its ordinary meaning and refers to a location situated next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Lastly, the term "anterior" has its ordinary meaning and refers to a location ahead of or to the front of another location.

The terms "rigid," "flexible," "compliant," and "resilient" may be used to distinguish characteristics of portions of certain features of the orthopedic device. The term "rigid" should denote that an element of the device is generally devoid of flexibility. Within the context of frame or support members or shells that are "rigid," it is intended to indicate that they do not lose their overall shape when force is applied, and in fact they may break if bent with sufficient force. The term "flexible" should denote that features are capable of repeated bending such that the features may be bent into retained shapes or the features do not retain a general shape, but continuously deform when force is applied.

The term "compliant" may be used to qualify such flexible features as generally conforming to the shape of another object when placed in contact therewith, via any suitable natural or applied forces, such as gravitational forces, or forces applied by external mechanisms, for example, strap mechanisms. The term "resilient" may be used to qualify such flexible features as generally returning to an initial general shape without permanent deformation. As for the term "semi-rigid," this term may be used to connote properties of support members or shells that provide support and are free-standing; however such support members or shells may have some degree of flexibility or resiliency.

C. Various Embodiments of the Strap Tightener Assembly

As illustrated in FIG. 1, an embodiment of a strap tightener assembly 10 is described in an exemplary combination with an unloading, osteoarthritic knee brace 11 of a type generally described in U.S. Pat. No. 7,198,610. The description focuses on the structure, materials, and configuration of a strap tightener assembly, without belaboring the effects and modalities for treating osteoarthritis in the knee joint and a brace structure itself.

Figure 2:
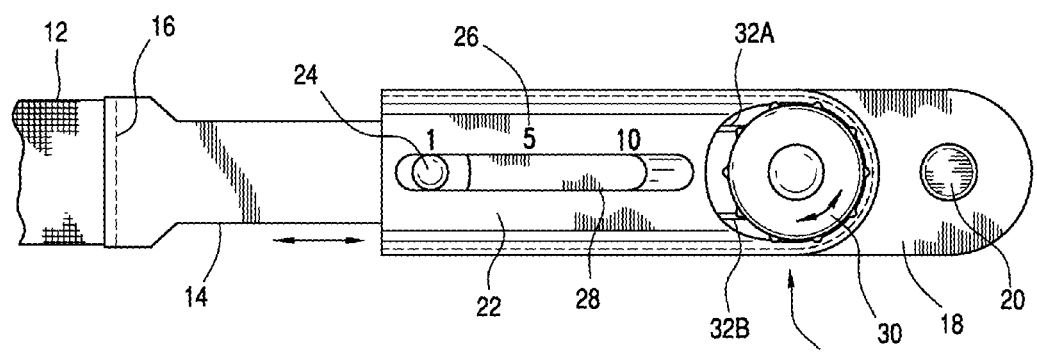
FIG. 2 is a plan view of an embodiment of a strap tightener assembly.
Figure 3:
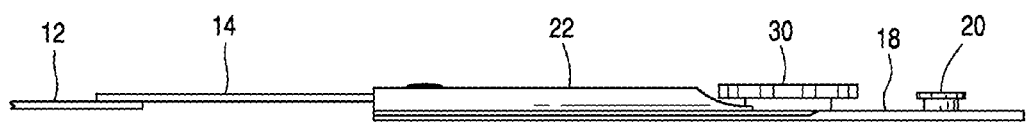
FIG. 3 is an elevational view of the embodiment of FIG. 2.

Turning to FIGS. 1-3, the strap tightener assembly 10 includes a strap 12 secured to a strap assembly or tab 14 having an elongate configuration by a plurality of stitches 16 or other suitable means. The tab 14 is slidably connected to a base 18 within a channel formed by the base 18 and a cover 22. The tab 14 carries a retaining element 24 at one end portion, such as a protrusion, that slidably engages a slot 28 formed by the cover 22. The cover 22 defines indicia 26 along the slot 28 to indicate relative tension in the strap 12 with the retaining element 24 serving as an indicator.

A tightening device 30 is mounted onto the base 18, and engages the tab 14. The tightening device 30 includes incremental, rotary movement at a plurality of predetermined settings which allows the strap 12 to be adjusted relative to the base in an incremental and predefined manner. According to this embodiment, a pair of cables 32A, 32B engages the tab 14 and the cables are wound or released from the tightening device permitting the incremental adjustment of the strap relative to the cover 22.

An example of a tightening device is found in U.S. Pat. No. 7,992,261, incorporated in its entirety by reference, and in U.S. Pat. No. 7,198,610.

As exemplified in FIG. 1, the base 18 carries a locking or engaging element 20 which is securable at an opening 36 formed on a frame member 34 of the brace 11. According to this exemplary embodiment, the strap 12 crosses another strap 40, and both the straps 12, 40 connect to both upper and lower frame members 34, 38 of the orthopedic device such that the straps 12, 40 exert forces F against the knee.

The strap is preferably formed from a textile based material, but can be constructed from a variety of materials such as polymers and combinations of polymers and textiles. The tab is preferably constructed from a flexible, polymeric material having sufficient rigidity to slide within the channel formed by the base and cover. The base is preferably formed from a polymeric material having greater rigidity than the tab, whereas the cover can be constructed from a polymeric material or textile. In a preferred embodiment, the base and the cover are interlockingly secured to one another.

As shown in FIG. 1, the strap tightener assembly may be considered substantially flexible and resilient by having at least a majority of its length which can yield to the shape of a wearer's anatomy as the strap is tightened thereagainst. According to FIG. 1, while some components, such as the tightening device may not be or have less flexibility than the base and the cover, the strap tightener assembly when considered as a whole can flex about the leg of the wearer as the strap is tightened. Upon release of tension, the strap tightener assembly is sufficiently resilient to return to its previous shape prior to tightening of the strap.

Figure 4:
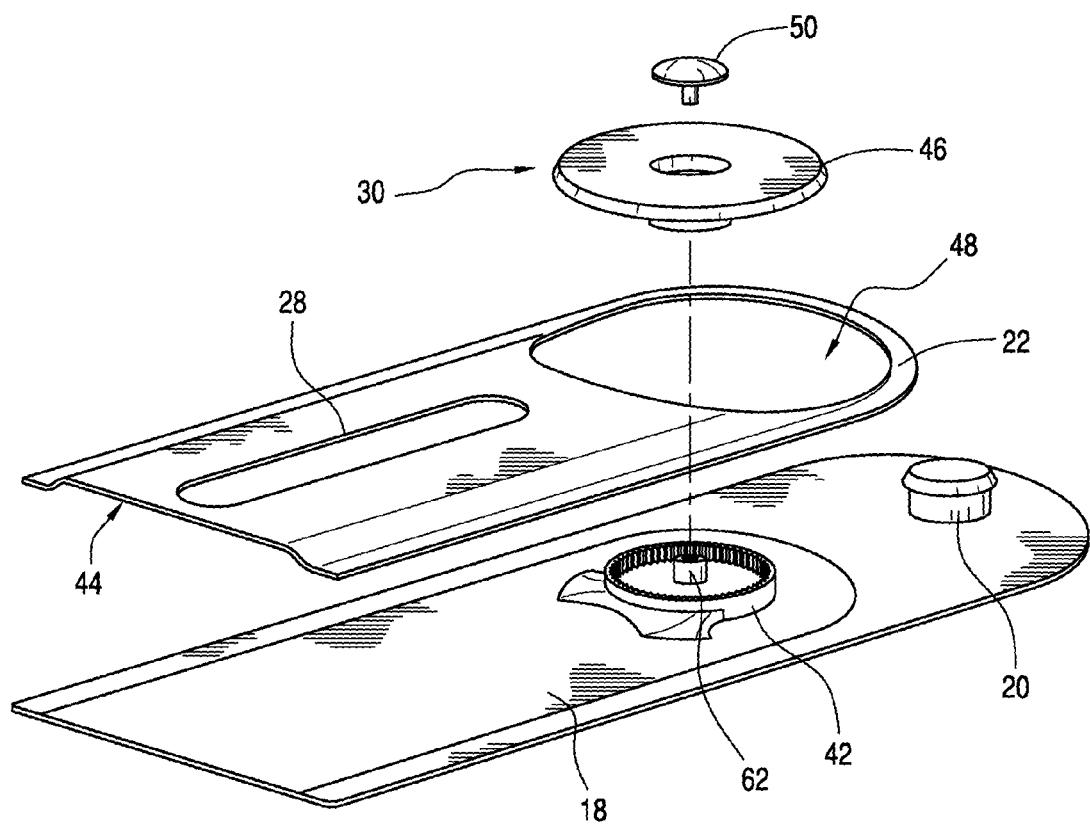
FIG. 4 is an exploded view of an embodiment of the strap tightener assembly.

Turning to FIG. 4, a channel 44 is shown as extending between the base 18 and the cover 22. According to this embodiment, the cover 22 forms an opening 48 through which a dial 46 of the tightening device 30 secures. The tightening device 30 includes a pin 50 connecting the dial 46 to the base 18, which forms a housing 42 bearing a series of teeth about its inner circumferential periphery and for receiving the tightening device 46. A detent (not shown) is provided in combination with the dial for engaging the teeth in order to form a ratcheting device. The dial 46 is configured to rotate about an axis 62 about which the pin 50 extends so that the detent engages the teeth.

Figure 5:
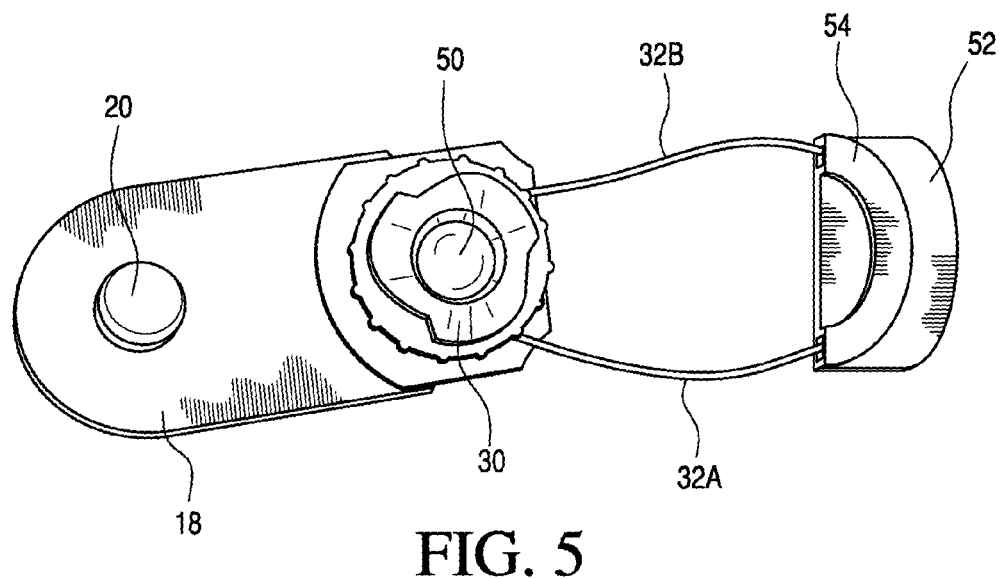
FIG. 5 is a perspective view of an embodiment of components of the strap tightener assembly.

In FIG. 5, the tightening device 30 includes the two cables 32A, 32B which secure to a cable retainer 52 which has a channel 54 adapted for retaining the cables 32A, 32B. The cable retainer 52 may be secured to the tab 14, to permit movement of the strap relative to the base, or alternatively, the cable guide 52 is arranged to slide within the channel formed by the base 18 and a cover 22.

Figure 6:
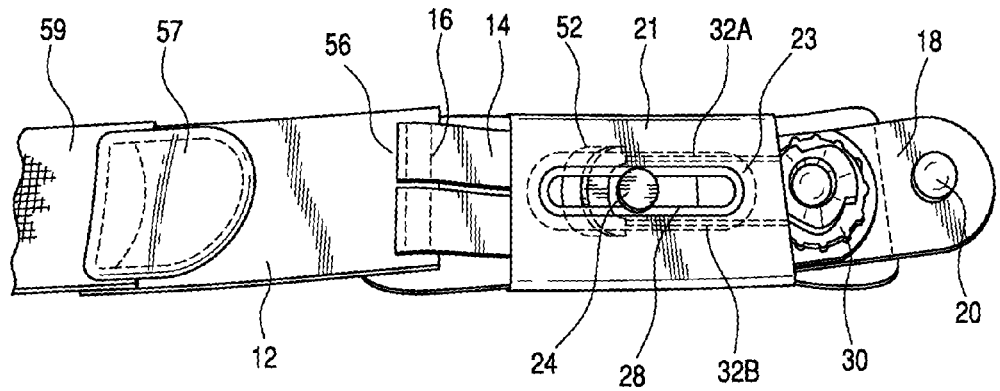
FIG. 6 is a perspective view of another embodiment of the strap tightener assembly.

Referring to FIG. 6, another embodiment of the strap tightener assembly 10 includes a textile based cover 21 having a reinforced edge 23 about the slot 28. FIG. 6 shows the position of the cable retainer 52 on the base 18 with the cables 32A, 32B. Also, according to this embodiment, a second end 57 of the strap 12 is shown as securing against the surface of the strap, with the first end 56 secured to the tab 14. The strap 12 is merely an intermediate strap coupling a main strap 59 to the strap tightener assembly 10. The strap 12 and the main strap 59 are trimmable so as to customize the length of the straps.

Figure 7A:
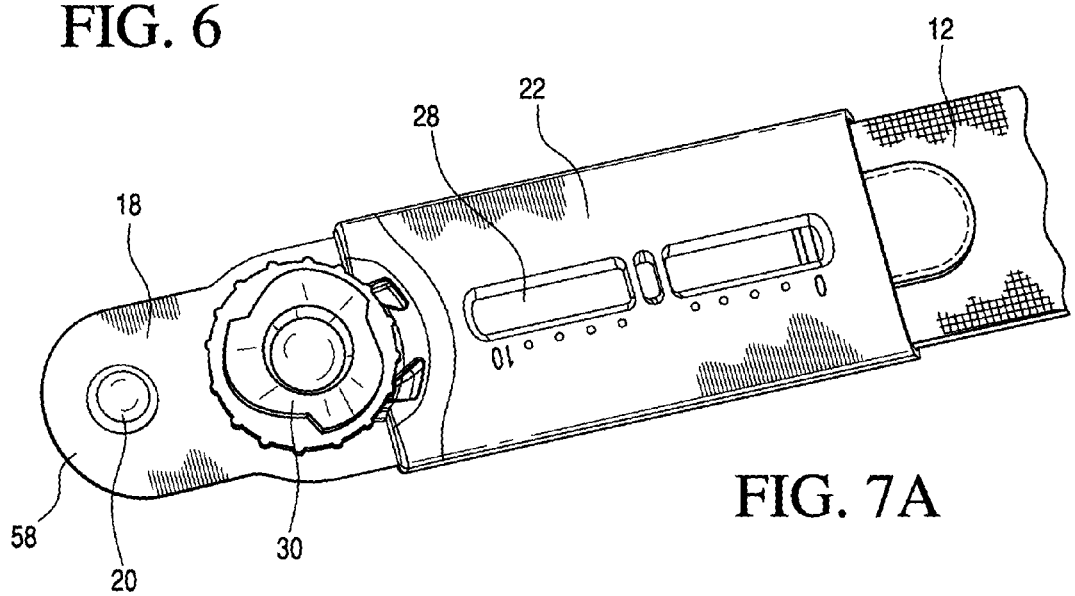
FIG. 7A is a perspective view of another embodiment of the strap tightener assembly.
Figure 7B:
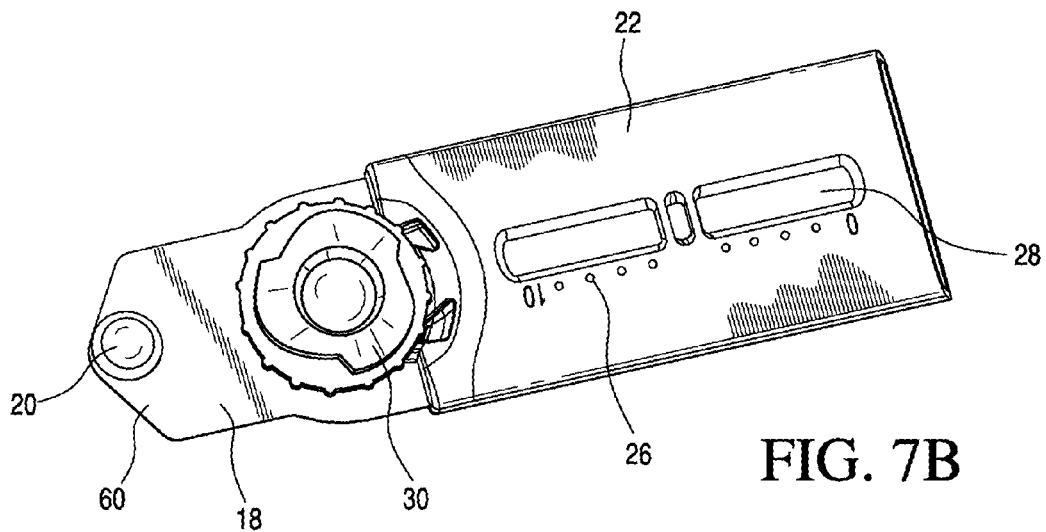
FIG. 7B is a perspective view of yet another embodiment of the strap tightener assembly without a strap attached thereto.

According to the embodiments of FIGS. 7A and 7B, the base 18 may have different shapes, as evidenced by the first end portion 58 of the base 18 in FIG. 7A, and the first end portion 60 of the base 18 in FIG. 7B.

FIGS. 8A-8D show an embodiment of the strap tightener assembly having a forward or first end portion profile 60 wherein the locking element 20 extends substantially at an edge. The housing 42 for the tightening device extends outside of the cover 22, with the pivot point 62 for the tightening device 30 forward the cover 22, such that an arcuate edge portion 64 of the cover 22 is located near the housing 42 at which the cover 22 forms first and second openings 65 for receiving the cable 32. A cable retainer 78 is secured to the strap 12, and cable 32, as in FIGS. 2 and 5. The cable retainer 78 is coupled to the tightening device 30 so the cable retainer 78 can slide within the channel formed by the base 18 and the cover 22 while carrying the strap 12.

FIG. 8A shows a series of windows 29 of the slot 28 which allows for an indicator 92 formed on the cable retainer 78 to show where the cable retainer 78 is relative to the cover 22. The indicator 92 may be appropriately colored to provide contrast relative to the cover 22, and the cable retainer 78 is adapted to slide within the channel (i.e., 44 in FIG. 4) along the indicia 0-10 or other appropriate range used.

FIGS. 8B-8D show how the cover 22 interlocks with the base 18. The base 18 includes a plurality of protrusions 66 on an under side of the base 18. Each protrusion 66 extends through openings 68 formed by the cover 22, and the protrusions engage edges surrounding the openings 68. Each protrusion 66 has a surface 70 upon which fastener elements may be secured so the strap tightener assembly may be secured to a sleeve having a loop covered surface. Padding 76, such as an elongate strip, is preferably secured to the underside of the base. For example, the padding 76 may be only located along the protrusions 66.

FIG. 8D shows the housing 42 as including openings 72, 74 through which cables connecting to the tightening device extend. Additional openings and structural features may be formed to guide the cables or permit mounting of additional components to the base.

Figure 8E:
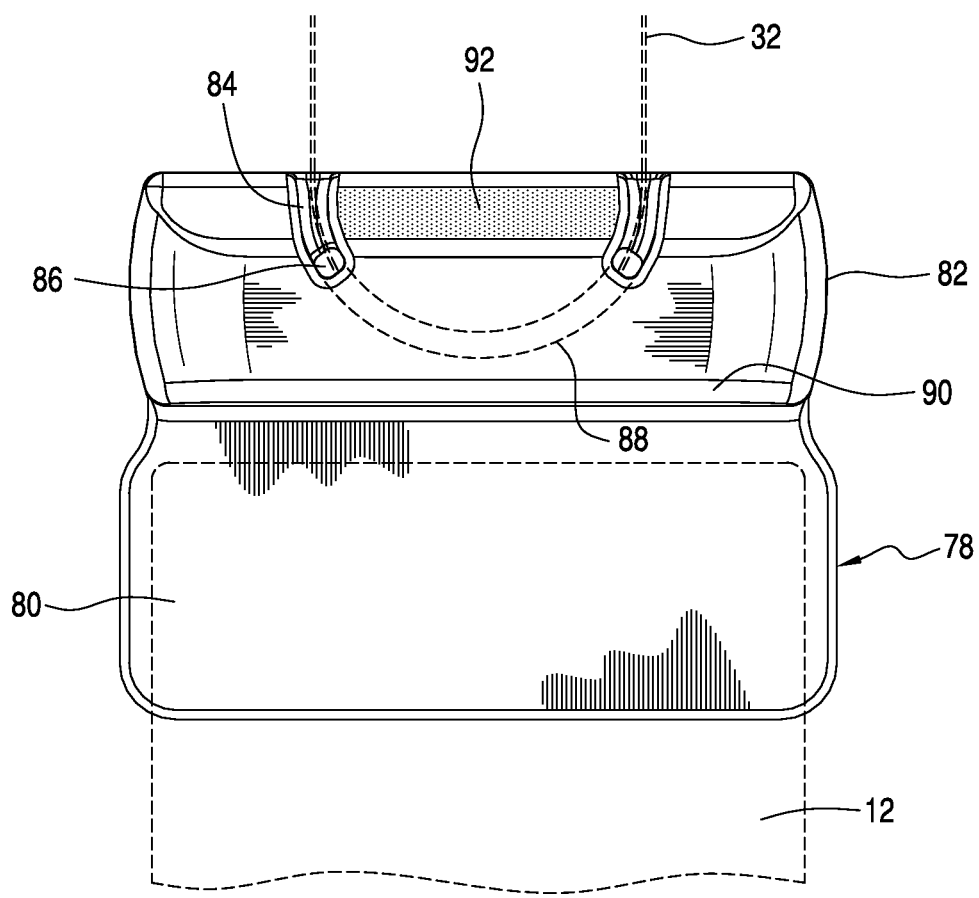
FIG. 8E is a plan frontal view of a cable retainer in FIG. 8A.

FIG. 8E illustrates the cable retainer 78 as having a strap extension 80 used to secure the strap 12 to the cable retainer 78. The strap may be stitched, adhered or mechanically locked to the strap extension 80. The strap extension is preferably formed as a flat, thin portion of the cable retainer having flexibility but preferably more rigidity than the strap mounted thereon. The strap extension is preferably at least of the same width as the strap.

Alternatively, the strap may be formed as a single piece with the cable retainer 78, such as by an injection molded construction. The cable retainer 78 also defines a base portion 82 which defines a channel 84 for guiding the cable 32 along the cable retainer 78. The channel 84 is recessed from the base portion 82, and defines opposed holes 86 through which a portion of the cable extends into a base portion 88 of the channel 84 which secures the cable to the cable retainer 78.

The indicator 92 is provided generally between the holes 86 and is adapted to be visible through the window 29 of the cover 22. The channel 84 includes recessed portion relative to the indicator 92 so the cable does not interfere with the indicator as the cable retainer is adjusted within the channel. The channel 84 is preferably centrally formed within the thickness of the cable retainer to maintain stable sliding within the channel, however other constructions may be used. The cable retainer 78 defines a ledge 90 dividing the base portion 82 from the strap extension 80 to at least in part to stably provide thickness for the base portion 82 with the cable, and allow for the strap extension 80 to have flexibility in combination with the strap 12.

The cable retainer is arranged to slide within the channel formed by the base and the sleeve to preferably maintain the cables within the channel, confining them to be covered by the sleeve. This arrangement is advantageous in that the user is not exposed to the cables which may be caught by objects. The windows of the slot preferably extend between the cables to again protect the cables from outside objects.

Preferably the base, cable, and cable retainer are inelastic and the strap itself, particularly when used in the embodiment of an osteoporosis knee brace. While the base or other components may be flexible, this is not to be confused with elastic which connotes stretching in length as opposed to bending as in flexible. Alternatively, however, the base may have some elasticity versus the strap, and any combination of the components and strap may be inelastic or elastic with varying degrees relative to one another.

The strap tightener of FIGS. 8A-8E is preferably arranged to yield to the shape of the leg or other anatomical portion of the wearer. Although some components by themselves may not be flexible, such as the tightening device 30, other parts may be flexible including the base and the cover, and at least portions of the cable retainer such as the strap extension.

Figure 9:
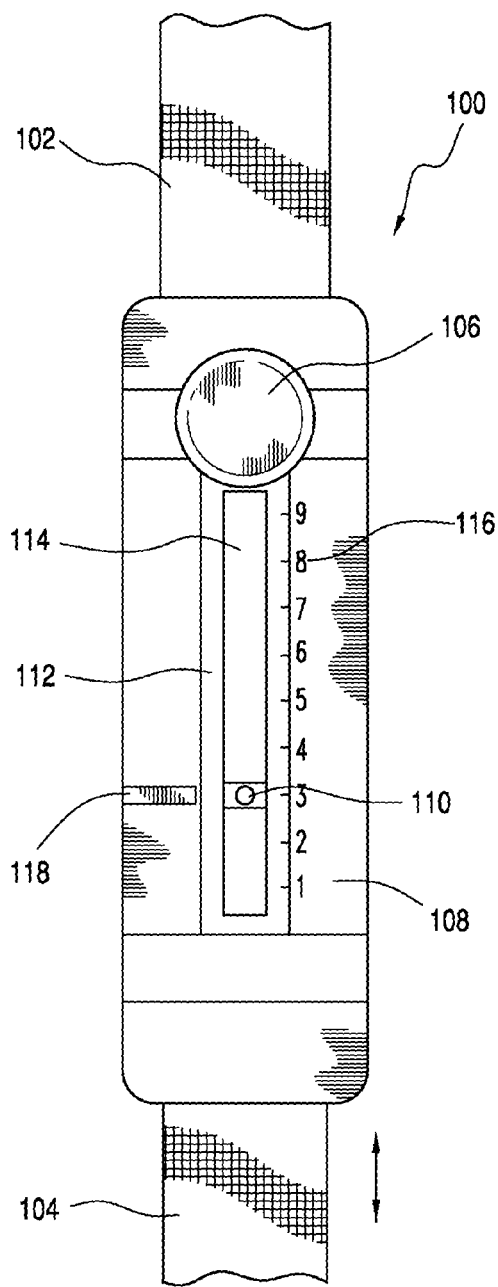
FIG. 9 is another embodiment of a strap tightener assembly.

In observing FIG. 9, yet another embodiment of a strap tightener assembly 100 is illustrated. According to this embodiment, the assembly 100 couples first and second strap segments 102, 104. The first strap segment 102 may secure to the cover 108 in a stationary manner. The assembly 100 includes a tightening device 106 that couples to the second strap segment 104 to allow adjustment of the second strap segment 104 relative to the cover 108. The cover 108 has a slot opening 114 formed about a central region or base area 112. A plurality of indicia 116 are located along the slot opening 114, and an indicator 110 is connected to the second strap segment 104 to enable an indication of travel of the second strap segment 104 relative to the cover 108.

Preferably the cover 108 includes padding on an underside to provide a comfortable interface against the wearer. The cover 108 may be flexible to yield to the anatomy of the wearer. The cover may likewise be formed from a rigid or semi-rigid material according to other applications.

The first strap segment 102 may engage the tightening device so turning or adjustment of the tightening device may cause both or only one of the first and second strap segments to travel relative to the cover.

A stripe or marking 118 may be added to the face of the cover 108 along the scale 116 to provide a marker for how much the tightening device should be tightened. According to a variation, the cover may be formed or covered with a hook-receivable material which allows adjustment in location of the stripe which has hook-type material. In an alternative variation, the cover may have a markable surface that permits a clinician to mark with a pen the appropriate location. In each variation, however, while not limited, it is desirable that the marking can be adjusted during treatment. Additional markings may be provided at any time which allows the clinician to set up "scaling over time" permitting the wearer to remove the marking after a level of treatment is completed.

Figure 10:
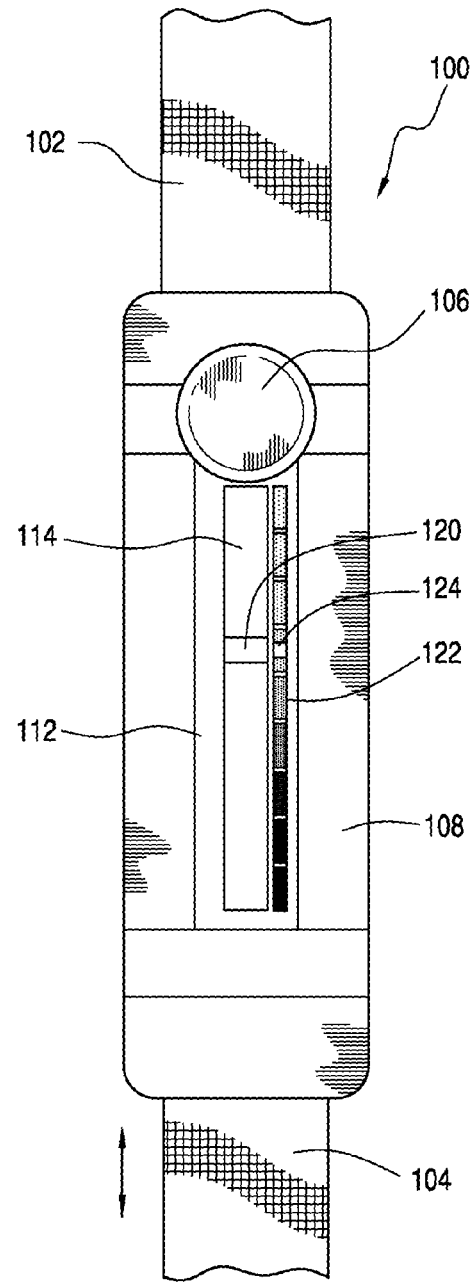
FIG. 10 is yet another embodiment of a strap tightener assembly.

Turning to FIG. 10, the strap tightener assembly may include a color scale 122 with an indicator 120 corresponding to the color scale. As an alternative to the marking located alongside the scale 122, a marker 124 may apply to the scale 122 itself to indicate a certain tightening level.

Figures 11, 12:
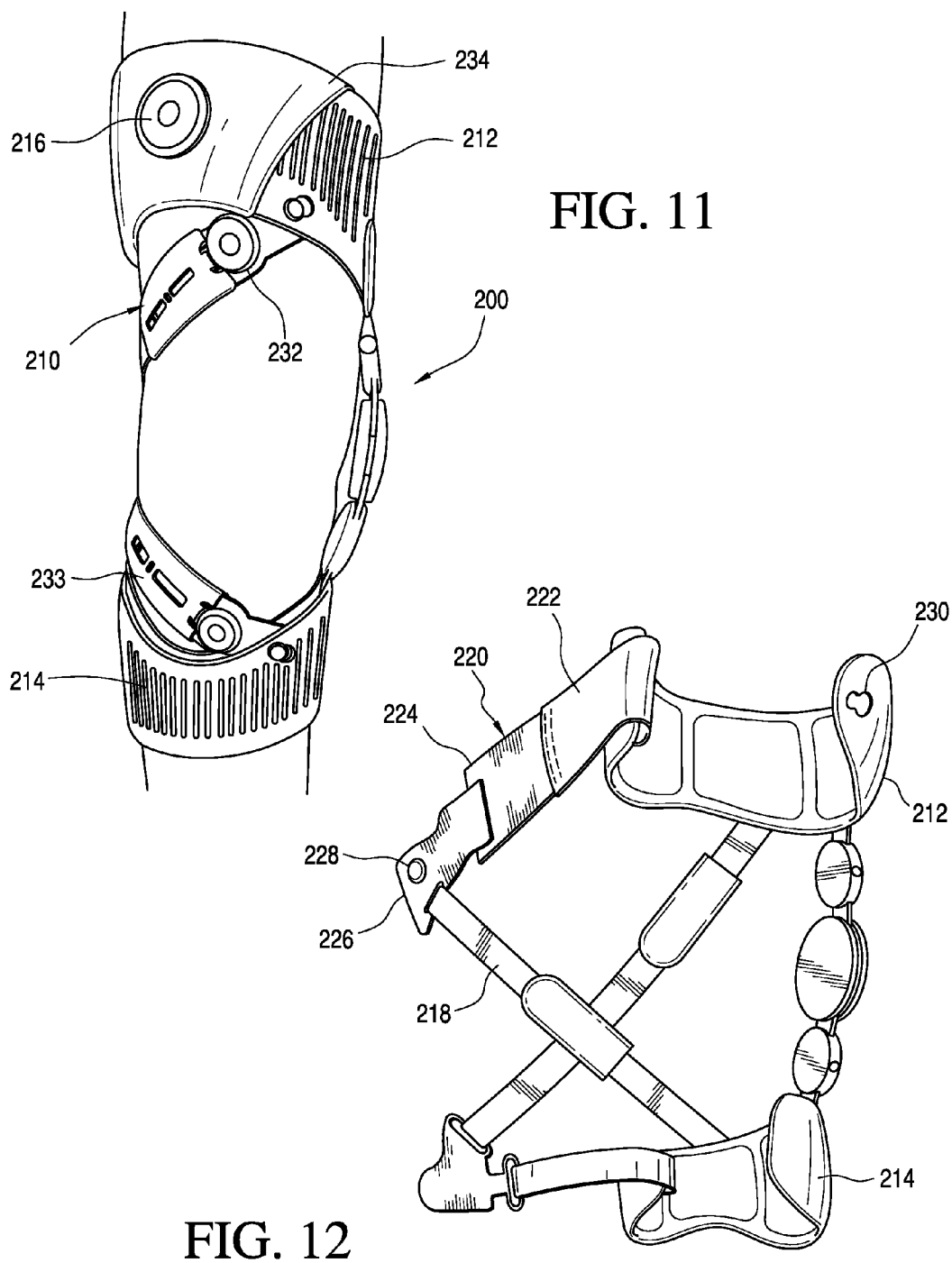
FIG. 11 is a perspective view showing an additional strap tightener assembly on the orthopedic device of FIG. 1.
FIG. 12 is a perspective view showing a rear side of the orthopedic device according to FIG. 11.

In reference to FIG. 11, an additional strap tightener assembly 210 may be used in any part of the orthopedic device 200, and particular for circumferentially adjusting a strap. A tightening device 232 may be secure on a frame member 212 and adjustably secure to a strap assembly or a strap 220 which is connected to the same frame member 212 or another frame member 214. By adjusting the tightening device 232, the strap assembly or the strap 220 can be tightened or loosened accordingly.

Figure 13:
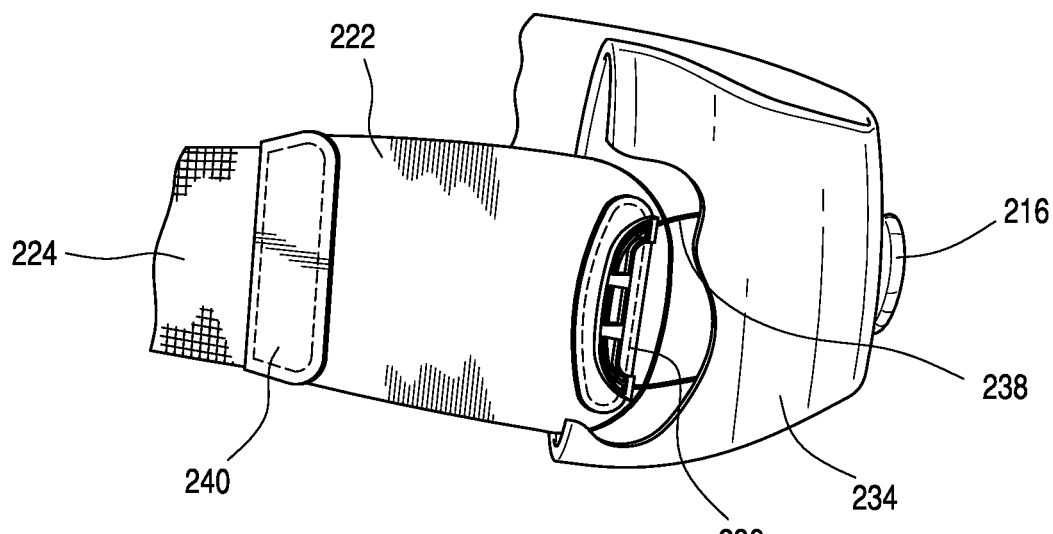
FIG. 13 is a schematic view showing partial exposure of the additional strap tightener assembly of FIG. 11.

FIGS. 12 and 13 depict a variation of the strap assembly 220 includes a first strap segment 222 secured to a cable retainer 236 which connects to a cable 238 engaging the tightening device 216, and a second strap segment 224 is adjustably secured to the first strap segment 222. Substantial adjustments can be made by securing the second strap segment 224 to various locations on the first strap segment 222, or vice versa, and then small adjustments may be made by the tightening device 216 such that either the first and second strap segments have corresponding hook and loop fastening elements, or equivalent fastening elements.

The first and second strap segments are detachably secured to one another by locking elements. For example, strap segment 222 has a hook receivable surface, and the second strap segment 224 has a hook tab 240 engageable over the hook receivable surface. The first and second strap segments may be constructed from different materials and having different properties such as being elastic, inelastic and varying degrees therebetween.

In reference to FIG. 12, the second strap segment 224 adjustably secures to a bracket 226 having a fastening element 228 which is engageable with an opening 230 formed on a first side of the frame member 212. The strap assembly 220 extends generally from a second side of the frame member and connects to the first side to form a circumferential attachment for a leg of a wearer. A diagonal or supplementary strap 218 may likewise be secured to the bracket 226 under orthopedic device embodiments incorporated by reference.

The first or the second strap segments may have different elasticities or be wholly inelastic. The first strap segment may be inelastic, whereas the second strap segment may be elastic. This allows for some tensioning relief on the leg of the wearer, particularly since the second strap segment may be substantially longer than the first strap segment which may not reach beyond or reaches minimally beyond the first frame member periphery. This allows for most of the circumferential distance between the first and second sides of the frame member to be spanned by the elastic second strap segment. The lack of elasticity of the first strap segment is advantageous since it carries the cable retainer.

It follows from this embodiment that small adjustments in tightening can be achieved after the strap assembly is secured to the wearer's leg. The elasticity of the second strap segment allows for compensation of the leg as it goes between flexion and extension. This arrangement will also accommodate a variety of leg circumferences.

Because most adjustment of the strap assembly is achieved by adjusting the second strap segment relative to the first strap segment, and the attachment of the bracket to the frame member, the strap assembly can be fine tuned by the wearer but not outside of a range of initial fitting of the strap assembly by the methods associated between the first and second strap segments and the bracket discussed above, and the length of the cable. This allows for the wearer to make adjustments without having to tinker with the strap assembly and the bracket, and permits the practitioner to set the length of the strap assembly without the need for the wearer to make later adjustments, other than by the tightening device.

FIGS. 11 and 13 show that a sleeve 234 may be provided over at least a portion of the frame member. The sleeve protects the cable and prevents the cable from catching on environmental items.

Figure 14:
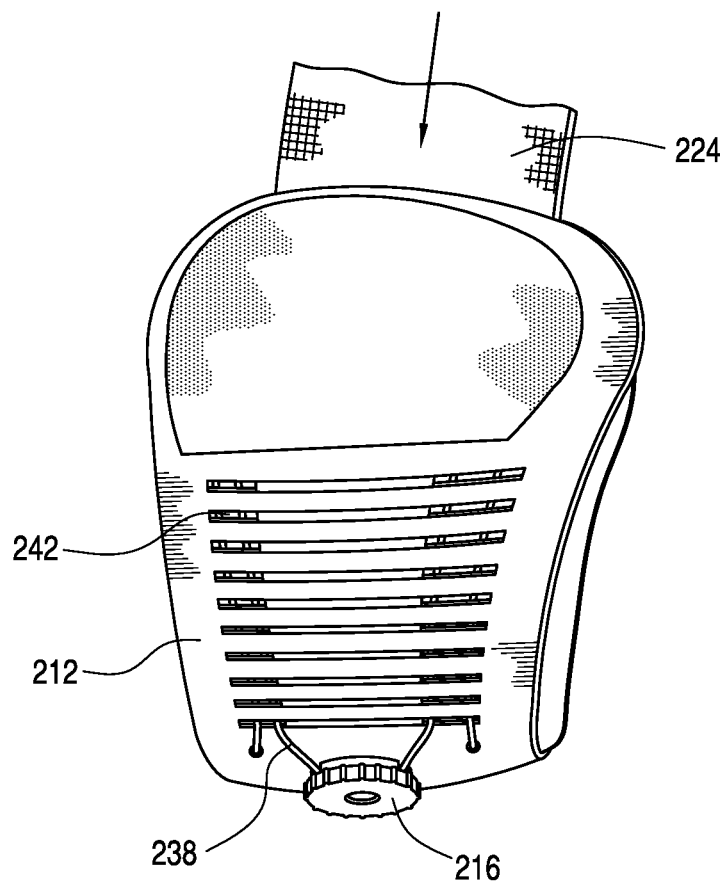
FIG. 14 is a variation of the additional strap tightener assembly of FIG. 13.

Turning to the embodiment of FIG. 14, the cable 238 connecting the tightening device 216 may be concealed by at least a portion of the frame member 212 or the cable may extend through portions 242 of the frame member 212.

While the foregoing embodiments have been described and shown, alternatives and modifications of these embodiments, such as those suggested by others, may be made to fall within the scope of the disclosure. Any of the principles described may be extended to any other orthopedic devices or other types of articles requiring similar functions of those structural elements described.

The invention claimed is:

1. A strap tightener assembly, the assembly comprising:
a base being flexible and having first and second ends;
a tightening device mounted on the base near the first end and movable relative thereto, the tightening device having incremental control at a plurality of predefined settings;
a strap assembly having a first end coupled to the tightening device and arranged to move linearly relative to the base from the second end to the first end by adjustment of the tightening device;
a cover having first and second ends with the first end facing the tightening device and the second receiving the strap assembly, the cover extending over the strap assembly and connected to the base, the base and the cover forming a channel permitting movement of the strap assembly therethrough, the cover defining an elongate slot extending along a portion of a length of the cover, the strap assembly having an indicator identifying the relative location of the strap assembly to the cover;
a cable rotatably secured and windable about the tightening device, the cable securing to the first end to the strap assembly;
wherein the strap assembly further comprises a cable retainer secured to the cable and the strap assembly is mounted to the cable retainer, the cable retainer defining first and second holes and a channel through which the cable extends, the cable retainer arranged to slide and be maintained within the channel formed between the cover and the base;
wherein the tightening device extends outside the cover with a pivot point for the tightening device, the tightening device having a housing defining first and second openings facing the cover through which the cable extends into the channel formed between the cover and the base, and about the cable retainer.

2. The strap tightener assembly according to claim 1, wherein the indicator slidably fits within the elongate slot of the cover.

3. The strap tightener assembly according to claim 1, wherein the cover includes a plurality of indicia representing a scale along a path which the indicator slides.

4. The strap tightener assembly according to claim 1, wherein the strap is formed from a textile-based material.

5. The strap tightener assembly according to claim 1, wherein the first end of the base defines a forward end profile to the strap tightener assembly and a locking element perpendicularly protrudes from the base;
wherein the tightening device extends outside the cover with a pivot point for the tightening device located forward the cover between a first end of the cover and the locking element.

6. The strap tightener assembly according to claim 1, wherein the first and second openings of the housing are spaced apart from one another and directed parallel to one another facing the first end of the cover.

* * * * *